(12) United States Patent
Schmaus et al.

(10) Patent No.: US 7,119,123 B2
(45) Date of Patent: Oct. 10, 2006

(54) ANTIMICROBIALLY ACTIVE 4-METHYL-4-ARYL-2-PENTANOLS, THEIR PREPARATION AND USE

(75) Inventors: Gerhard Schmaus, Höxter-Bosseborn (DE); Holger Joppe, Dassel (DE)

(73) Assignee: Symrise GmbH & Co. KG, Holzminden (DE)

( * ) Notice: Subject to any disclaimer, the term of this patent is extended or adjusted under 35 U.S.C. 154(b) by 163 days.

(21) Appl. No.: 10/790,770

(22) Filed: Mar. 3, 2004

(65) Prior Publication Data
US 2004/0171698 A1    Sep. 2, 2004

(51) Int. Cl.
*A61K 31/045* (2006.01)
(52) U.S. Cl. .................. 514/730; 514/712; 514/718; 568/55; 568/648; 568/715; 568/718; 568/812; 568/813
(58) Field of Classification Search ............ 568/812, 568/648, 715, 813, 55, 763; 514/712, 717, 514/730, 718
See application file for complete search history.

(56) References Cited

U.S. PATENT DOCUMENTS 2,850,410 A * 9/1958 Manly .................. 127/70
4,321,257 A * 3/1982 Sipos ................... 424/78.06

FOREIGN PATENT DOCUMENTS

| EP | 0 032 659 A1 | 1/1981 |
| FR | 1526791 A * | 4/1968 |
| GB | 1105455 A * | 3/1968 |
| WO | WO 96/19428 | 6/1996 |

OTHER PUBLICATIONS

CA 62:69211 (1961).
CA 92:185719 (1980).

* cited by examiner

*Primary Examiner*—Thurman K. Page
(74) *Attorney, Agent, or Firm*—Roylance, Abrams, Berdo & Goodman, L.L.P.

(57) ABSTRACT

Antimicrobially active 4-methyl-4-aryl-2-pentanols of the Formula 1 below, methods for the preparation of these compounds and their use as antimicrobial active compounds are described.

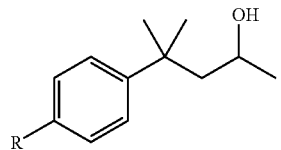

Surprisingly, compounds of the Formula 1 for which: R=hydrogen, hydroxyl, alkoxy group with up to 10 C atoms, straight-chain or branched, saturated or unsaturated alkyl with up to 10 C atoms, alkylthioether group with up to 10 C atoms, the alkylthioether group being bonded to the aromatic ring via a thioether bridge, fluorine, chlorine, bromine, iodine, or alkyl with up to 10 C atoms that is interrupted by one or more oxygen and/or sulphur atoms, have proved to be antimicrobially active.

29 Claims, No Drawings

ANTIMICROBIALLY ACTIVE 4-METHYL-4-ARYL-2-PENTANOLS, THEIR PREPARATION AND USE

The present invention relates to antimicrobially active 4-methyl-4-aryl-2-pentanols of Formula 1 below, methods for the preparation of these compounds and their use as antimicrobial active compounds.

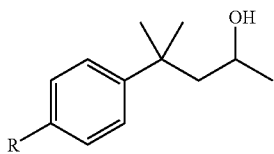

Surprisingly, compounds of the Formula 1 for which: R=
hydrogen,
hydroxyl,
alkoxy group with up to 10 C atoms,
straight-chain or branched, saturated or unsaturated alkyl with up to 10 C atoms,
alkylthioether group with up to 10 C atoms, the alkylthioether group being bonded to the aromatic ring via a thioether bridge,
fluorine, chlorine, bromine, iodine, or
alkyl with up to 10 C atoms that is interrupted by one or more oxygen and/or sulphur atoms, have proved to be antimicrobially active.

Each of these compounds, as well as mixtures thereof, are suitable as antimicrobial active compounds or active compound mixtures
(a) for the cosmetic treatment of microorganisms causing dandruff,
(b) for the cosmetic treatment of microorganisms causing body odour,
(c) for the cosmetic treatment of microorganisms causing acne,
(d) for the cosmetic treatment of microorganisms causing mycoses,
(e) for the treatment of microorganisms on or in inanimate material, and/or
(f) for the preservation of perishable articles.

The human skin is populated by a multiplicity of different bacteria. The majority of these bacteria are not pathogenic and are irrelevant for the physiological state of the skin and for its odour. Others, on the other hand, can have a decisive influence on the healthy state of the skin. Some microorganisms which have a substantial influence on human skin flora are given in Table 1.

TABLE 1

| Microorganisms: | Situs of Population |
| --- | --- |
| *Staphylococcus epidermidis* | underarm odour, body odour in general |
| *Staphylococcus aureus* | atopic eczemas; wound infection |
| *Corynebacterium xerosis* | underarm odour |
| *Brevibacterium epidermidis* | underarm odour; foot odour |
| *Propionibacterium acnes* | acne |
| *Escherichia coli* | wound infection |
| *Pseudomonas aeruginosa* | wound infection |
| *Malassezia furfur* (syn. *Pityrosporum ovale*) | development of dandruff |
| *Candida albicans* | general candidoses |

TABLE 1-continued

| Microorganisms: | Situs of Population |
| --- | --- |
| *Trichophyton mentagrophytes* | skin and nail mycoses |
| *Trichophyton rubrum* | skin and nail mycoses |
| *Epidermophyton floccosum* | skin and nail mycoses |
| *Aspergillus niger* | mould infestation |

As a result of the bacterial degradation of substances produced in the body and contained in perspiration, such as, for example, unsaturated fatty acids, decomposition products with an unpleasant odour that can have a severe effect on bodily wellbeing are formed from precursors that have a more or less weak odour. In cosmetics, products that either suppress the formation of body perspiration (so-called antiperspirants) or substances that inhibit the growth of the bacteria of the human skin that are responsible for odour formation (deodorants) are used to prevent the formation of the substances responsible for body odour. Species of bacteria such as *Staphylococcus epidermidis, Corynebacterium xerosis* and *Brevibacterium epidermidis* generally have decisive responsibility for the formation of underarm and foot odour or body odour. In the cosmetics industry there is therefore an ongoing need for new agents for the treatment of microorganisms causing this and other body odour (including underarm and foot odour).

A microorganism that causes acne is *Propionibacterium acnes*, which is a germ that grows anaerobically. The cosmetics industry is continually looking for agents for the treatment of this germ and other microorganisms that cause acne.

All areas of the human skin can be infested by mycoses (in particular dermotomycoses and nail mycoses). Areas of the skin on which moisture and warmth can build up as a result of wearing clothing, shoes or jewellery are particularly frequently affected. Fungus diseases of the fingernail and toenail regions are experienced as being particularly unpleasant. Various species of *Trichophyton* and *Epidermophyton* frequently have decisive responsibility for the formation of mycoses. The cosmetics industry is continuously searching for novel agents for the treatment of microorganisms causing these and other mycoses.

In addition, in the field of hair care there is an intensive search for substances for the treatment of the germ *Malassezia furfur*, which has decisive responsibility for the development of dandruff, and of other microorganisms causing dandruff.

Within the context of the present text, "treatment" is understood to be any form of influence on the microorganisms concerned by means of which the reproduction of these microorganisms is inhibited and/or the microorganisms are killed.

Furthermore, there is a continual need in the cosmetics and pharmaceutical industry for agents for the preservation of cosmetic or pharmaceutical articles that otherwise are perishable.

When searching for corresponding antimicrobially active and/or preservative agents, it must be taken into account that the substances used in cosmetic and/or pharmaceutical products must be
  toxicologically acceptable,
  well tolerated by the skin,
  stable (in particular in the customary cosmetic and/or pharmaceutical formulation),
  preferably odourless and inexpensive to produce (i.e. using standard methods and/or starting from standard precursors).

The search for suitable (active) substances that possess one or more of the said characteristics to an adequate extent is made more difficult for the person skilled in the art because there is no clear dependence between the chemical structure of a substance, on the one hand, and its biological activity vis-à-vis specific microorganisms (germs) and its stability, on the other hand. Furthermore, there is no predictable relationship between the antimicrobial action, the toxicological acceptability, tolerance by the skin and/or the stability.

The aim of the present invention was, therefore, to indicate an antimicrobial active compound that is active at least against one microorganism, but preferably against several of the microorganisms discussed above, and preferably also meets one or more of the subsidiary conditions mentioned.

Surprisingly, it has now been found that the initially mentioned 4-methyl-4-aryl-2-pentanols with the indicated meanings for the radical R possess outstanding antimicrobial properties and are active against a whole series of microorganisms.

Amongst the said compounds of the Formula 1, the compounds 4-methyl-4-phenyl-2-pentanol (CA numbers 2035-93-0, 2R/S mixture; 329313-22-6, 2R isomer and 329313-20-4, 2S isomer) and 4-methyl-4-p-cumenyl-2-pentanol (CA number: 93963-35-0); R=i-propyl) are known. However, an antimicrobial activity of the said substances has not been reported hitherto. In addition, it is known from J. Dental Res. 40,384 (1961) that 4-methyl-4-phenyl-2-pentanol has a certain glycolysis-inhibiting action, which is why this substance is suitable as a cariostatic active substance. However, an antimicrobial activity of the said substances has not been reported hitherto.

The alcohols of the Formula 1 have a powerful antimicrobial action against microorganisms on the human skin that form odour and can thus be used as deodorants as an excellent alternative to or as a supplement to known antimicrobial active compounds (such as, for example farnesol) in cosmetic products and the like. The compounds of the Formula 1 according to the invention also have a good effect against *Propionibacterium acnes, Malassezia furfur* and germs that causes mycoses, such as, for example, *Trichophyton mentagrophytes* so that they can also be used for the treatment (control) of acne, as anti-dandruff agents or in the treatment of mycoses (in particular dermatomycoses). Because of their broad spectrum of action and in particular because of their activities against Gram-negative bacteria such as *Escherichia coli* and *Pseudomonas aeruginosa* as well, against yeasts such as *Candida albicans* and against fungi such as *Aspergillus niger*, the compounds of the Formula 1 according to the invention are also excellent agents for the preservation of, for example, cosmetic and/or pharmaceutical formulations.

The concentration in which an alcohol of the Formula 1 according to the invention is used in a cosmetic end product (for example a cream, a shampoo or the like) is preferably in the range between 0.0069 and 20% (m/m), preferentially in the range between 0.05 and 5% (m/m), in each case based on the total mass of the cosmetic product.

In a preferred method for the cosmetic and/or therapeutic treatment of (a) microorganisms causing dandruff, (b) microorganisms causing body odour, (c) microorganisms causing acne and/or (d) microorganisms causing mycoses, an antimicrobially effective amount of one or more of the compounds of the Formula 1 according to the invention is applied topically to the human or animal body, so that the growth of the microorganism or organisms that may be present is inhibited and/or these organisms are killed. Such amounts are generally in the range between 0.0069 and 20% (m/m), preferably in the range between 0.05 and 5% (m/m), in each case based on the total mass of the product.

However, the compounds of the Formula 1 according to the invention are, of course, not only intended for application to the human or animal body, but, for example, are also suitable (e) for the treatment of microorganisms on or in inanimate material as well as (f) for the preservation of perishable articles. Formulations for antimicrobial treatment of surfaces are generally in the range between 0.0069 and 20% (m/m), preferably in the range between 0.05 and 5% (m/m), in each case based on the total mass of the applied product.

A substance of the Formula 1 according to the invention can also be used as a constituent of perfume compositions (fragrance compositions) and, for example, impart an antimicrobial action to a perfumed end product. A particularly preferred perfume composition comprises (a) a perfume in an amount that has a sensory effect, (b) one or more compounds of the Formula 1 (where R can have any of the meanings indicated above) in an amount that has a preservative effect and (c) optionally one or more excipients and/or additives. Since the proportion of perfume in a cosmetic end product is frequently in the region of approximately 1% (m/m), a perfume which contains a compound of the Formula 1 according to the invention, will preferably consist of approximately 5–50% (m/m) of one or more compounds of the Formula 1. It has proved particularly advantageous that the substances of the Formula 1 have only a weak inherent odour or are even completely odourless; since this characteristic predestines them for use as preservatives in a perfume composition.

The invention also relates to antimicrobial formulations that also contain, in addition to (a) an antimicrobially effective amount of one or more compounds of the Formula 1 according to the invention (where R can have any of the meanings indicated above), also (b) a carrier substance that is compatible with component (a). The specific carrier substance that is employed will include water, aqueous gels, aqueous creams, oil-in-water emulsions, and other carriers readily selectable by the exercise of no more than the existing level of skill in the art for the particular formulation and intended use.

Further aspects of the present invention can be seen from the appended patent claims and the following examples.

1. Synthesis of 4-methyl-4-aryl-2-pentanols of the general Formula 1

EXAMPLE 1

Synthesis of (R,S)-4-methyl-4-phenyl-2-pentanol (Equation 1; Formula 2)

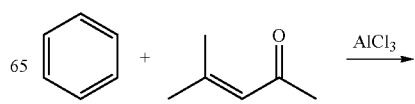

-continued

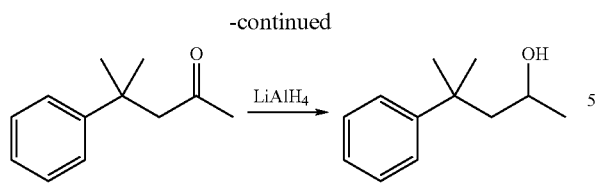

Equation 1 a) Friedel-Crafts acylation of benzene with mesityl oxide 110.4 g (0.83 mol) aluminium chloride are initially introduced into a 2 l stirrer (sic). 360 ml (3.4 mol) benzene are then added. 68.6 g (0.7 mol) mesityl oxide are added dropwise with stirring and cooling at approximately 10° C. The reaction batch is stirred for a further 20 h. The aluminium complex is then hydrolysed with 100 ml water at a temperature of at most 20° C. The aqueous phase is separated off in a separating funnel. Washing is then carried out with a further 100 ml water. The organic phase is separated off and washed with aqueous sodium hydroxide solution until neutral. Excess benzene is distilled off. Crude yield: 180 g; yield of 4-methyl-4-phenyl-2-pentanone: 165 g; purity: 96%.

b) Reduction of 4-methyl-4-phenyl-2-pentanone with LiAlH$_4$ 50 ml absolute THF and 1.5 g LiAlH$_4$ (39.5 mmol) are initially introduced into a 250 ml flask. 18.5 g 4-methyl-4-phenyl-2-pentanone (105 mmol) dissolved in 10 ml absolute THF are added dropwise at approximately 0° C. to 5° C. The reaction batch is stirred for a further 1 h. The excess LiAlH$_4$ is then hydrolysed by adding water. After saponification with 10% NaOH, washing until neutral and distilling off the solvent, approximately 18 g (R,S)-4-methyl-4-phenyl-2-pentanol is obtained: purity 97%.

Spectroscopic data for (R,S)-4-methyl-4-phenyl-2-pentanol (Formula 2): $^{13}$C (CDCl$_3$; 75.5 MHz): δ (ppm)=25.0 (q), 29.3 (q), 29.6 (q), 37.0 (s), 53.5 (t), 65.5 (d), 125.7 (d), 125.8 (2d), 128.2 (2d), 148.8 (s); MS: m/z (%)=178 (–, M+), 160 (5), 145 (8), 120 (45), 119 (100), 118 (8), 117 (7), 105 (10), 91 (49), 79 (10), 78 (6), 77 (5).

EXAMPLE 2

Synthesis of (R,S)-4-methyl-4-p-tolyl-2-pentanol, (Equation 2; Formula 3)

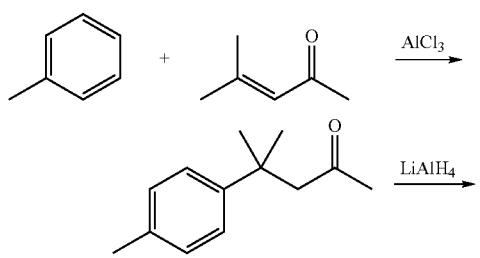

Equation 2 a) Friedel-Crafts acylation of toluene with mesityl oxide 110.4 g (0.83 mol) aluminium chloride are initially introduced into a 2 l stirrer (sic). 312 g (3.4 mol) toluene are then added. 68.6 g (0.7 mol) mesityl oxide are metered in with stirring and cooling. The reaction batch is stirred for a further 20 h. The reaction batch is then further processed analogously to Example 1. Crude yield: 115g; yield of 4-methyl-4-p-tolyl-2-pentanone: 86 g (purity: 94%).

b) Reduction of 4-methyl-4-p-tolyl-2-pentanone with LiAlH$_4$ 50 ml absolute THF and 1.5 g LiAlH$_4$ (39.5 mmol) are initially introduced into a 250 ml flask. 20 g 4-methyl-4-p-tolyl-2-pentanone (105 mmol) dissolved in 10 ml absolute THF is added dropwise at approximately 0° C. to 5° C. The reaction batch is stirred for a further 1 h. The excess LiAlH$_4$ is then hydrolysed by adding water. After saponification with 10% NaOH, washing until neutral and distilling off the solvent, approximately 21 g (R,S)-4-methyl-4-p-tolyl-2-pentanol (purity: 92%) is obtained.

Spectroscopic data for (R,S)-4-methyl-4-p-tolyl-2-pentanol (Formula 3): $^{13}$C (CDCl$_3$; 75.5 MHz): δ (ppm)=20.8 (q), 24.9 (q), 29.0 (q), 30.0 (q), 36.7 (s), 53.5 (t), 65.5 (d), 125.7 (2d), 129.0 (2d), 135.1 (s), 145.7 (s); MS: m/z (%)=192 (7, M+), 134 (29), 133 (100), 119 (10), 117 (6), 115 (6), 105 (27), 93 (7), 91 (9), 85 (1), 77 (3).

EXAMPLE 3

Synthesis of (R,S)-4-methyl-4-p-cumenyl-2-pentanol (Equation 3; Formula 4)

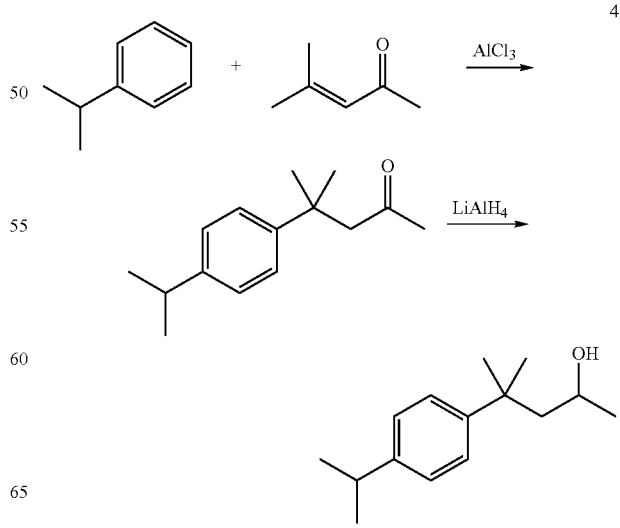

Equation 3:

a) Friedel-Crafts acylation of cumene with mesityl oxide 110.4 g (0.83 mol) aluminium chloride are initially introduced into a 2 l stirrer flask. 408 g (3.4 mol) cumene are then added. 68.6 g (0.7 mol) mesityl oxide are metered in with stirring and cooling. The reaction batch is stirred for a further 20 h. The reaction batch is then further processed analogously to Example 1. Crude yield: 415 g; yield of 4-methyl-4-p-cumenyl-2-pentanone: 22 g (purity: 87%).

b) Reduction of 4-methyl-4-p-cumenyl-2-pentanone with LiAlH$_4$ 50 ml absolute THF and 0.5 g LiAlH$_4$ (13.2 mmol) are initially introduced into a 250 ml flask. 10 g 4-methyl-4-p-cumenyl-2-pentanone (45.8 mmol) dissolved in 10 ml absolute THF are added dropwise at approximately 0° C. to 5° C. The reaction batch is stirred for a further 1 h. The excess LiAlH$_4$ is then hydrolysed by adding water. After saponification with 10% NaOH, washing until neutral and distilling off the solvent, 9 g (R,S)-4-methyl-4-p-cumenyl-2-pentanol (purity: 85%) is obtained.

Spectroscopic data for (R,S)-4-methyl-4-p-cumenyl-2-pentanol (Formula 4): $^{13}$C (CDCl$_3$; 75.5 MHz): δ (ppm)= 24.0 (2q), 24.8 (q), 29.0 (q), 30.0 (q), 33.4 (d), 36.7 (s), 53.6 (t), 65.4 (d), 125.7 (2d), 126.3 (2d), 145.9 (s), 146.0 (s); MS: m/z (%)=220 (6, M+), 162 (22), 161 (100), 145 (7), 133 (4), 131 (4), 119 (20), 115 (3), 105 (8), 91 (11), 77 (2).

EXAMPLE 4

Synthesis of (R,S)-4-methyl-4-(4-n-butylphenyl)-2-pentanol, (Equation 4), Formula 5

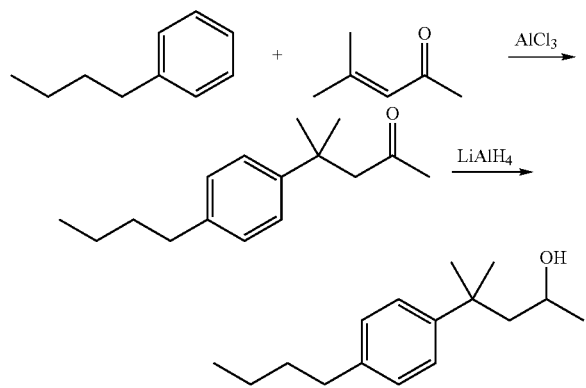

Equation 4:

a) Friedel-Crafts acylation of n-butylbenzene with mesityl oxide 110.4 g (0.83 mol) aluminium chloride are initially introduced into a 2 l stirrer flask. 480 g (3.1 mol) n-butylbenzene are then added. 68.6 g (0.7 mol) mesityl oxide are metered in with stirring and cooling. The reaction batch is stirred for a further 20 h. The reaction batch is then further processed analogously to Example 1. Crude yield: 441 g; yield of 4-methyl-4-(4-n-butylphenyl)-2-pentanone: 60 g (purity: >80%).

b) Reduction of 4-methyl-4-(4-n-butylphenyl)-2-pentanone with LiAlH$_4$ 50 ml absolute THF and 0.3 g LiAlH$_4$ (7.9 mmol) are initially introduced into a 250 ml flask. 5 g 4-methyl-4-(4-n-butylphenyl)-2-pentanone (21 mmol) dissolved in 5 ml absolute THF is added dropwise at approximately 0° C. to 5° C. The reaction batch is stirred for a further 1 h. The excess LiAlH$_4$ is then hydrolysed by adding water. After saponification with 10% NaOH, washing until neutral and distilling off the solvent, 4 g (R,S)-4-methyl-4-p-cumenyl-2-pentanol (purity: >80%) is obtained.

Spectroscopic data for (R/S)-4-methyl-4-(4-n-butylphenyl)-2-pentanol (Formula 5): $^{13}$C (CDCl$_3$; 75.5 MHz): δ (ppm)=14.0 (q), 22.4 (t), 24.9 (q), 28.8 (q), 30.2 (q), 33.6 (t), 35.1 (t), 36.7 (s), 53.7 (t), 65.6 (d), 125.7 (2d), 128.4 (2d), 140.3 (s), 145.7 (s); MS: m/z (%)=234 (4, M+), 176 (25), 175 (100), 161 (2), 147 (3), 131 (6), 119 (17), 105 (5), 91 (12), 77 (2), 57 (8), 45 (7), 41 (7).

2. Experiments to determine the antimicrobial action of 4-methyl-4-aryl-2-pentanols The finding that 4-methyl-4-aryl-2-pentanols of the Formula 1 (where R can have any of the meanings indicated above) are very particularly suitable for controlling germs that are responsible for body odours goes back to a series of experiments in which the particularly relevant germs *Staphylococcus epidermidis, Corynebacterium xerosis* and *Brevibacterium epidermidis* were investigated. However, not only the results for the inhibition of *Staphylococcus epidermidis, Corynebacterium xerosis* and *Brevibacterium epidermidis,* but also the results of further tests, are indicated below. Specifically, it has been found that the activity of the said 4-methyl-4-aryl-2-pentanols is also surprisingly high against further test germs such as *Malassezia furfur, Trichophyton mentagrobytesbytes, Propionibacterium acnes, Candida albicans* and *Aspergillus niger,* as a result of which further field of application result.

2.1. General Test Conditions:

The antimicrobial action of the substances synthesised according to Examples 1–4 (Formulae 2–5) was demonstrated with the aid of the agar dilution method based on DIN 58 940/ICS and DIN 58 944/ICS. Petri dishes 5.5 cm in diameter were charged with 8.7 ml freshly prepared Mueller-Hinton agar (Merck, Ref. 1.05437 or Wilkins-Chalgren agar boillon (sic), Oxoid, Ref. CM 643, supplemented with 10 g agar-agar/liter) kept liquid at 50° C., to which the various concentrations of the diluted samples were added in 3.3% (V/V)=0.3 ml. Mueller-Hinton agar that contained 3% Tween80 (Merck, Ref. 8.22 187) was used for the test germ *Malassezia furfur.*

2.6 ml of the 3.3% samples were diluted with ethanol (96%; Merck, Ref. 1.00971). The further test concentrations of the particular dilution series, which were prepared in the form of geometric series, were prepared by progressive 2:1 dilution with ethanol (96%).

By means of a further dilution with the test agar (0.3 ml sample or corresponding dilutions+8.7 ml agar), 30 times lower final concentrations were achieved in each case (corresponds to an initial concentration of 1100 ppm in each case). The concentrations indicated below relate to the pure substance and have been converted to ppm. Two agar plates were poured per test concentration and nutrient medium.

The following experiments were carried out with 2 agar plates in each case:

| | |
|---|---|
| K1: 9.0 ml Mueller-Hinton agar | (not inoculated) |
| K2: 8.7 ml Mueller-Hinton agar + 0.3 ml ethanol (96%) | (not inoculated) |
| K3: 8.7 ml Mueller-Hinton agar + 0.3 ml ethanol (96%) | (inoculated) |
| K4: 9.0 ml Mueller-Hinton agar | (inoculated) |
| K5: 9.0 ml Mueller-Hinton agar + 3% Tween80 | (not inoculated) |
| K6: 9.0 ml Mueller-Hinton agar + 3% Tween80 + 0.3 ml ethanol (96%) | (not inoculated) |
| K7: 9.0 ml Mueller-Hinton agar + 3% Tween80 + 0.3 ml ethanol (96%) | (inoculated) |
| K8: 9.0 ml Mueller-Hinton agar + 3% Tween80 | (inoculated) |
| K9: 9.0 ml Wilkins-Chalgren agar | (not inoculated) |
| K10: 9.0 ml Wilkins-Chalgren agar + 0.3 ml ethanol (96%) | (not inoculated) |
| K11: 9.0 ml Wilkins-Chalgren agar + 0.3 ml ethanol (96%) | (inoculated) |
| K12: 9.0 ml Wilkins-Chalgren agar | (inoculated) |

After solidification and drying (approximately 1 h at 37° C.), the test plates were inoculated in point form with, in each case, 1 µl of the test germ suspensions listed in the examples below. To check purity and identity, the bacteria (*Brevibacterium epidermidis*, *Corynebakterium* (sic) *xerosis*, *Staphylococcus aureus*; *Staphylococcus epidermidis*) which grow aerobically, were [lacuna] on Columbia blood agar (BioMérieux, Ref. 43049). The mould *Aspergillus niger*, the yeast *Candida albicans* and the skin fungus *Trichophyton mentagrophytes* were cultivated on Sabouraud agar (BioMérieux, Ref. 43555). *Malassezia furfur* was cultured on Sabourad-HLT agar with inhibitors (addition of Tween80: 1%; lecithin: 0.3%; histidine: 0.1%; Merck, Ref. 1.18368). *Propionibacterium acnes* was cultivated on Schaedler agar (BioMérieux, Ref. 43273). Further data on the test germs can be taken from Table 1.

TABLE 1

Test germs (strain names) and germ counts

| Test germ | Strain name | CFU*/7 ml |
|---|---|---|
| Brevibacterium epidermidis | ATCC 35514 | $2.8 \times 10^7$ |
| Corynebacterium xerosis | ATCC 7711 | $1.9 \times 10^7$ |
| Propionibacterium acnes | ATCC 11829 | $2.3 \times 10^8$ |
| Staphylococcus epidermidis | ATCC12228 | $2.9 \times 10^7$ |
| Malassezia furfur | DSM 6171 | $2.8 \times 10^7$ |
| Aspergillus niger | ATCC 16404 | $1.7 \times 10^7$ |
| Trichophyton mentagrophtes | CBS 26379 | $2.5 \times 10^7$ |
| Candida albicans | ATCC 10231 | $2.0 \times 10^7$ |

CFU* = colony-forming units

The preparation of the test germ suspensions of the bacterial germs that grow aerobically was carried out by incubation of Mueller-Hinton broth (Merck, Ref. 1.10293) which had been inoculated with a few individual colonies of the relevant test germs, at 36° C. After a distinct turbidity had been obtained, sterile nutrient broth was added to the suspensions in such an amount that the turbidity thereof corresponded to McFarland Standard 0.5 (approx. $1.5 \times 10^8$ CFU/ml).

For preparation of the other test germ suspensions, the test strains were cultured on the abovementioned solid nutrient medium, harvested using sterile swabs and taken up or diluted in such an amount of Mueller-Hinton broth that the turbidity of the suspensions corresponded to McFarland standard 0.5.

All test germ suspensions with the exception of *Propionibacterium acnes* were diluted again 1:10 with sterile broth and the germ count thereof was determined by the surface method using a Spiralometer (results: see Table 1).

The inoculated plates were incubated under the conditions indicated in Table 2 and then evaluated. The MIC (minimum inhibitory concentration) was regarded as the lowest concentration of active compound at which macroscopically there is no growth. Minimal, barely visible growth or few small individual colonies were evaluated as inhibition.

TABLE 2

Inoculation and incubation

| Test germ | Strain name | Growth condition | Nutrient medium | Incubation |
|---|---|---|---|---|
| Brevibacterium epidermidis | ATCC 35514 | Aerobic | Mueller-Hinton agar | 18 h at 36° C. |
| Corynebacterium xerosis | ATCC 7711 | Aerobic | Mueller-Hinton agar | 18 h at 36° C. |
| Propionibacterium acnes | ATCC 11829 | Anaerobic | Wilkins-Chalgren agar | 72 h at 36° C. |
| Candida albicans | ATCC 10231 | Aerobic | Mueller-Hinton agar | 48 h at 30° C. |
| Staphylococcus epidermidis | ATCC 12228 | Aerobic | Mueller-Hinton agar | 18 h at 36° C. |
| Malassezia furfur | DSM 6171 | Aerobic | Mueller-Hinton agar + 3% Tween 80 | 72 h at 30° C. |
| Trichophyton mentagrophytes | CBS 26379 | Aerobic | Mueller-Hinton agar | 72 h at 30° C. |
| Aspergillus niger | ATCC 16404 | Aerobic | Mueller-Hinton agar | 48 h at 30° C. |

2.2. MIC values of (R/S)-4-methyl-4-aryl-2-pentanols

The MIC values of various (R/S)-4-methyl-4-aryl-2-pentanols were determined in accordance with the general test conditions described under 2.1. (c.f. Table 3; MIC values for (R/S[lacuna]-4-methyl-4-phenyl-2-pentanol, for (R/S)-4-methyl-4-p-tolyl-2-pentanol, (R/S)-4-methyl-4-p-cumenyl-2-pentanol and (R/S)-4-methyl-4-(4-n-butylphenyl)-2-pentanol).

TABLE 3

MIC values for (R/S)-4-methyl-4-phenyl-2-pentanol 2; (R/S)-4-methyl-tolyl-2-pentanol 3; (R/S)-4-methyl-4-p-cumenyl-2-pentanol 4 and (R/S)-4-methyl-4-(4-n-butylphenyl)-2-pentanol 5

| Microorganism | 2 | 3 | 4 | 5 |
|---|---|---|---|---|
| Staphylococcus epidermidis | 1100 | 550 | 138 | 1100 |
| Corynebacterium xerosis | 1100 | 275 | 69 | 69 |
| Brevibacterium epidermidis | 1100 | 550 | 138 | 550 |
| Propionibacterium acnes | 1100 | 550 | 138 | >1100,1 |
| Malassezia furfur | 69 | 69 | 550 | 550 |
| Trichophyton mentagrophytes | 550 | 138 | 69 | 69 |
| Candida albicans | 1100 | 1100 | >1100 | >1100 |
| Aspergillus niger | 550 | 550 | >1100 | >1100 |
| Escherichia coli | >1100 | >1100 | >1100 | >1100 |
| Pseudomonas aeruginosa | >1100 | >1100 | >1100 | >1100 |

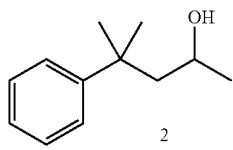

2

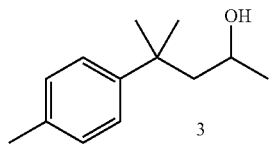

3

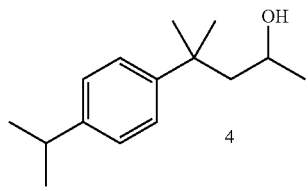

4

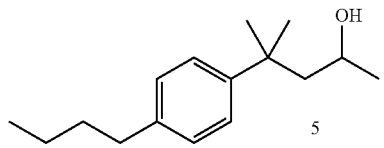

5

Clear inhibition of the growth of Gram-positive bacteria causing body odour, such as Staphylococcus epidermidis, Corynebacterium xerosis, Brevibacterium epidermidis, could be observed for all substances listed in Table 3, even in concentrations of less than 0.15%. In this context (R/S)-4-methyl-4-p-cumenyl-2-propanol showed the strongest activity (Staphylococcus epidermidis: 138 ppm=138 µg/ml; Corynebacterium xerosis: 69 ppm=69 µg/ml; Brevibacterium epidermidis: 138 ppm=138 µg/ml). The activity against Propionibacterium acnes, which is responsible for acne, likewise particularly pronounced in the case of (R/S)-4-methyl-4-p-cumenyl-2-propanol (138 ppm=138 µg/ml), although an activity can also be observed in the case of substances 2, 3 and 5. On the other hand, (R/S)-4-methyl-4-phenyl-2-propanol (Formula 2) and (R/S)-4-methyl-4-p-tolyl-2-propanol are the most effective substances against yeasts such as Candida albicans and moulds. Since the said substances or also mixtures of the substances have a very broad spectrum of action, they can also be used as preservatives.

It is pointed out that, in the context of the present text, the general term (R/S)-4-methyl-4-aryl-2-pentanol (Formula 1) comprises both the 2S-configured enantiomers and also the 2R-configured enantiomers as well as arbitrary mixtures of 2S- and 2R-configured 4-methyl-4-aryl-2-pentanols. It is true that, for commercial reasons, it is particularly advantageous to use the racemates of the particular alcohols to inhibit the growth of microorganisms since these are particularly readily accessible by synthesis. However, the pure enantiomers or non-racemic mixtures of said enantiomers are also suitable for the purposes according to the invention.

An important field of application for (R/S)-4-methyl-4-aryl-2-pentanols of the Formula 1 is the inhibition of the bacteria responsible for the development of body odour (including underarm odour and foot odour) (in particular Staphylococcus, Corynebacterium and Brevibacterium species). In addition, (R/S)-4-methyl-4-aryl-2-pentanols can be used to inhibit skin and nail fungi that cause mycoses (dermatomycoses, nail mycoses; Trichophyton and Epidermophyton species), to inhibit microorganisms responsible for the development of dandruff (Malassezia furfur, syn.; Pityrosporum ovale or P. orbiculare) and for the treatment of acne (inhibition of the growth of Propioibacterium acnes). Furthermore, an activity against fungi such as Aspergillus niger and yeasts such as Candida albicans as well, and also in concentrations of >1100 ppm also against Gram-negative bacteria such as, for example, Escherichia coli or Pseudomonas aeruginosa also enables the (R/S)-4-methyl-4-aryl-2-pentanols of the Formula 1 that have been described to be used as preservatives.

Mixtures of active compounds containing (a) an antimicrobial (R/S)-4-methyl-4-aryl-2-pentanol of the Formula 1 or (b) several substances of the Formula 1 are as a rule applied topically in the form of solutions, creams, lotions, gels, sprays or the like, in particular insofar as they are used against germs causing body odour. For other purposes, an oral (tablets, capsules, powders, drops), intravenous, intraocular, intraperitoneal or intramuscular administration or application in the form of an impregnated bandage is sensible in some cases.

The concentration of the active compounds (R/S)-4-methyl-4-aryl-2-pentanols of the Formula 1 in the formulations applied (topically) is preferably in the range of 0.0069%–20% (m/m) and preferentially in the range of 0.05%–0.5% (m/m). In this context the antimicrobial active compound complex can be used (a) prophylactically or (b) as needed.

The concentration of the amount of active substance that is, for example, to be applied daily is variable and depends on the physiological condition of the test person as well as on parameters specific to the individual, such as age or body weight. (R/S)-4-methyl-4-aryl-2-pentanols of the Formula 1 can be used either on their own, as mixtures or also in combination with further antimicrobially active substances.

The invention claimed is:

1. Method for the cosmetic and/or therapeutic treatment of (a) microorganisms causing dandruff, (b) microorganisms causing body odour, (c) microorganisms causing acne and/or (d) microorganisms causing mycoses, comprising:

topically applying to a human or animal body suffering from (a) microorganisms causing dandruff, (b) microorganisms causing body odour, (c) microorganisms causing acne and/or (d) microorganisms causing mycoses, an antimicrobially active amount of one or more compounds of the Formula 1

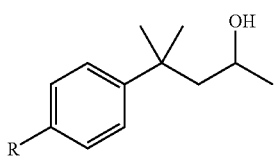

wherein R=hydrogen, hydroxyl, alkoxy group with up to 10 C atoms, straight-chain or branched, saturated or unsaturated alkyl with up to 10 C atoms, alkylthioether group with up to 10 C atoms, the alkylthioether group being bonded to the aromatic ring via a thioether bridge, fluorine, chlorine, bromine, iodine, or alkyl with up to 10 C atoms that is interrupted by one or more oxygen and/or sulphur atoms.

2. A method for controlling microorganisms by applying to a microbial population comprising microorganisms that cause dandruff an antimicrobially active composition that comprises a compound according to Formula 1

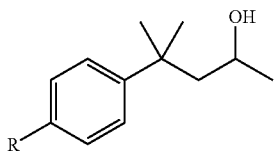

where R=
hydrogen,
hydroxyl,
alkoxy group with up to 10 C atoms,
straight-chain or branched, saturated or unsaturated alkyl with up to 10 C atoms,
alkylthioether group with up to 10 C atoms, the alkylthioether group being bonded to the aromatic ring via a thioether bridge,
fluorine, chlorine, bromine, iodine, or
alkyl with up to 10 C atoms that is interrupted by one or more oxygen and/or sulphur atoms.

3. A method for controlling microorganisms by applying to a microbial population comprising microorganisms that cause body odour an antimicrobially active composition that comprises a compound according to Formula 1

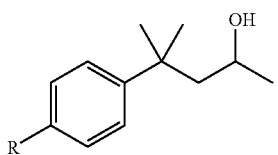

where R=
hydrogen,
hydroxyl,
alkoxy group with up to 10 C atoms,
straight-chain or branched, saturated or unsaturated alkyl with up to 10 C atoms,
alkylthioether group with up to 10 C atoms, the alkylthioether group being bonded to the aromatic ring via a thioether bridge,
fluorine, chlorine, bromine, iodine, or
alkyl with up to 10 C atoms that is interrupted by one or more oxygen and/or sulphur atoms.

4. A method for controlling microorganisms according to claim 3 by applying said antimicrobially active compound to a microbial population comprising microorganisms that grow aerobically.

5. A method for controlling microorganisms by applying to a microbial population that comprises *Propionibacterium acnes* an antimicrobially active composition that comprises a compound according to Formula 1

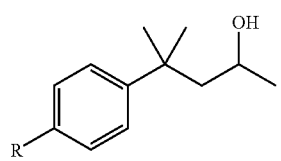

where R=
hydrogen,
hydroxyl,
alkoxy group with up to 10 C atoms,
straight-chain or branched, saturated or unsaturated alkyl with up to 10 C atoms,
alkylthioether group with up to 10 C atoms, the alkylthioether group being bonded to the aromatic ring via a thioether bridge,
fluorine, chlorine, bromine, iodine, or
alkyl with up to 10 C atoms that is interrupted by one or more oxygen and/or sulphur atoms.

6. A method for controlling microorganisms by applying said to a microbial population comprising microorganisms that cause mycoses an antimicrobially active composition that comprises a compound according to Formula 1

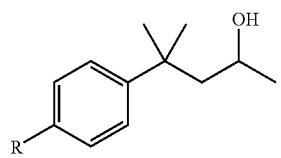

where R=
hydrogen,
hydroxyl,
alkoxy group with up to 10 C atoms,
straight-chain or branched, saturated or unsaturated alkyl with up to 10 C atoms,
alkylthioether group with up to 10 C atoms, the alkylthioether group being bonded to the aromatic ring via a thioether bridge,
fluorine, chlorine, bromine, iodine, or
alkyl with up to 10 C atoms that is interrupted by one or more oxygen and/or sulphur atoms.

7. A method according to claim 3 wherein R=hydrogen.

8. A method according to claim 1 wherein R=hydrogen.

9. A deodorant comprising the following components:
(a) an antimicrobially active amount of one or more compounds of the Formula 1

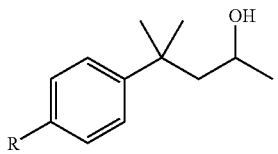

where R=
hydrogen,
hydroxyl,
alkoxy group with up to 10 C atoms,
straight-chain or branched, saturated or unsaturated alkyl with up to 10 C atoms,
alkylthioether group with up to 10 C atoms, the alkylthioether group being bonded to the aromatic ring via a thioether bridge,
fluorine, chlorine, bromine, iodine, or
alkyl with up to 10 C atoms that is interrupted by one or more oxygen and/or sulphur atoms as well as
(b) a carrier substance compatible with component (a).

10. A deodorant comprising a composition which is present in an amount sufficient to suppress growth of odor-causing bacteria on human skin, said composition comprising the following components:
(a) an antimicrobially active amount of one or more compounds of the Formula 1

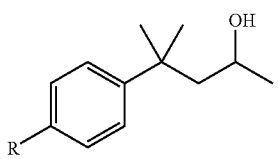

where R=
hydrogen,
hydroxyl,
alkoxy group with up to 10 C atoms,
straight-chain or branched, saturated or unsaturated alkyl with up to 10 C atoms,
alkylthioether group with up to 10 C atoms, the alkylthioether group being bonded to the aromatic ring via a thioether bridge,
fluorine, chlorine, bromine, iodine, or
alkyl with up to 10 C atoms that is interrupted by one or more oxygen and/or sulphur atoms as well as
(b) a carrier substance compatible with component (a).

11. A method according to claim 3 wherein said microorganism population includes a bacteria.

12. A deodorant according to claim 9 wherein said carrier comprises water, an aqueous gel, an aqueous cream, or an oil-in-water emulsion.

13. A deodorant according to claim 9 in the form of a topically applied cosmetic formulation.

14. A method according to claim 11 wherein said bacteria causes underarm or foot odor.

15. A method according to claim 14 wherein said bacteria causes underarm odor.

16. A deodorant according to claim 9 wherein said compound is present in an amount sufficient to control odor-causing bacteria on underarm human skin.

17. A deodorant according to claim 9 wherein said compound is present in an amount between 0.0069 and 20 wt % based on total weight.

18. A deodorant according to claim 9 wherein said compound is present in an amount between 0.05 and 5 wt % based on total weight.

19. A deodorant according to claim 9 wherein R=hydrogen.

20. A deodorant according to claim 9 wherein R=hydroxyl.

21. A deodorant according to claim 9 wherein
R=alkoxy group with up to C atoms, or straight-chain or branched, saturated or unsaturated alkyl with up to 10 C atoms.

22. A deodorant according to claim 9 wherein said carrier comprises water, an aqueous gel, an aqueous cream, or an oil-in-water emulsion.

23. A deodorant according to claim 10 wherein said compound is present in an amount between 0.0069 and 20 wt % based on total weight.

24. A deodorant according to claim 10 wherein said compound is present in an amount between 0.05 and 5 wt % based on total weight.

25. A deodorant according to claim 10 wherein R=hydrogen.

26. A deodorant according to claim 10 wherein R=hydroxyl.

27. A deodorant according to claim 10 wherein
R=alkoxy group with up to 10 C atoms, or straight-chain or branched, saturated or unsaturated alkyl with up to 10 C atoms.

28. A deodorant according to claim 10 wherein said carrier comprises water, an aqueous gel, an aqueous cream, or an oil-in-water emulsion.

29. A method according to claim 14 wherein said microorganism population comprises *Staphylococcus epidermidis, Corynebacterium xerosis* or *Brevibacterium epidermidis*.

* * * * *

UNITED STATES PATENT AND TRADEMARK OFFICE
CERTIFICATE OF CORRECTION

PATENT NO.       : 7,119,123 B2
APPLICATION NO.  : 10/790770
DATED            : October 10, 2006
INVENTOR(S)      : Gerhard Schmaus et al.

It is certified that error appears in the above-identified patent and that said Letters Patent is hereby corrected as shown below:

At Col. 6, line, 36 superscript the + sign     change "(%)=192 (7,M+)," to    --(%)=192 (7,M+),--

At Col. 7, line, 28 superscript the + sign     change "(%)=192 (7,M+)," to    --(%)=192 (7,M+),--

At Col. 8, line, 16 superscript the + sign     change "(%)=192 (7,M+)," to    --(%)=192 (7,M+),--

At Col. 8, line, 38     change (italicized) "phyton mentagrobytesbytes,"    to (italicized) --"phyton mentagrophytes,--

At Col. 10, line, 5     change "CFU*/7 ml"    to     --CFU*/ml--

---

CLAIMS:

At Col. 14, line 40    change    "said to a microbial"    to    --to a microbial--

At Col. 16, line 26    change    "with up to C atoms"    to    --with up to 10 C atoms--

Signed and Sealed this

Sixth Day of March, 2007

JON W. DUDAS
*Director of the United States Patent and Trademark Office*